United States Patent
Raghavan et al.

(10) Patent No.: US 6,464,662 B1
(45) Date of Patent: Oct. 15, 2002

(54) DRUG DELIVERY AND CATHETER SYSTEMS, APPARATUS AND PROCESSES

(75) Inventors: Raghu Raghavan, Baltimore, MD (US); Raju R. Viswanathan, Towson, MD (US); Timothy Poston, Singapore (SG)

(73) Assignee: Image-Guided Neurologics, Inc., Melbourne, FL (US)

( * ) Notice: Subject to any disclaimer, the term of this patent is extended or adjusted under 35 U.S.C. 154(b) by 124 days.

(21) Appl. No.: 09/626,059

(22) Filed: Jul. 26, 2000

(51) Int. Cl.[7] .............................................. A61M 1/00
(52) U.S. Cl. .............................. 604/28; 604/30; 604/27
(58) Field of Search ............................ 604/27, 19, 28, 604/30–34

(56) References Cited

U.S. PATENT DOCUMENTS

| | | | |
|---|---|---|---|
| 3,592,184 A | * | 7/1971 | Watkins et al. ............... 600/18 |
| 3,888,249 A | * | 6/1975 | Spencer ...................... 604/247 |
| 4,636,195 A | | 1/1987 | Wolinsky |
| 4,824,436 A | | 4/1989 | Wolinsky |
| 4,994,033 A | | 2/1991 | Shockey et al. |
| 5,021,044 A | | 6/1991 | Sharkawy |
| 5,049,132 A | | 9/1991 | Shaffer et al. |
| 5,087,244 A | | 2/1992 | Wolinsky et al. |
| 5,112,305 A | | 5/1992 | Barath et al. |
| 5,180,366 A | | 1/1993 | Woods |
| 5,181,911 A | | 1/1993 | Shturman |
| 5,197,946 A | | 3/1993 | Tachibana |
| 5,213,576 A | | 5/1993 | Abiuso et al. |
| 5,226,888 A | | 7/1993 | Arney |
| 5,254,089 A | | 10/1993 | Wang |
| 5,279,546 A | | 1/1994 | Mische et al. |
| 5,286,254 A | | 2/1994 | Shapland et al. |
| 5,295,962 A | | 3/1994 | Crocker et al. |
| 5,304,121 A | | 4/1994 | Sahatjian |
| 5,318,531 A | | 6/1994 | Leone |
| 5,336,178 A | | 8/1994 | Kaplan et al. |
| 5,354,291 A | | 10/1994 | Bales et al. .................... 604/35 |
| 5,364,356 A | | 11/1994 | Hofling |

(List continued on next page.)

FOREIGN PATENT DOCUMENTS

| | | | |
|---|---|---|---|
| EP | 0 406 901 A1 | 1/1991 | ............ A61M/5/00 |
| EP | 0 810 003 A2 | 12/1997 | .......... A61M/25/00 |
| WO | 9211890 | 7/1992 | |
| WO | WO 98/22175 | 5/1998 | .......... A61M/25/00 |

Primary Examiner—Timothy L. Maust
(74) Attorney, Agent, or Firm—Mark A. Litman & Assoc. P.A.

(57) ABSTRACT

A class of customizable injection devices or delivery instruments whose basic form is a stiff tube with holes of user-selectable size at several user-selectable places is described. The use of this device includes a method of selection and construction of a particular device from such a class of devices for a particular treatment procedure using computer-assisted means. Thus, the user may make selections among available or creatable choices (such as selection of hole size, selection of hole location, number of holes, etc.), and a method can be practiced for making such user-selection serve the goals of delivery of materials such as drugs, cells, or of devices sufficiently small and numerous to be delivered in fluid suspension. The tube should be relatively stiff in the sense that it deflects by no more than an amount between 0° and 15° under the stresses of insertion and placement at the end of a catheter, and varies less than 5 or less than 10% per cent in cross-sectional area when so deflected to the maximum of about 15 degrees.

12 Claims, 7 Drawing Sheets

U.S. PATENT DOCUMENTS

| | | | |
|---|---|---|---|
| 5,380,307 A | 1/1995 | Chee et al. .................. 604/264 |
| 5,385,547 A | 1/1995 | Wong et al. |
| 5,415,636 A * | 5/1995 | Forman .................. 604/101.03 |
| 5,498,236 A | 3/1996 | Dubrul et al. |
| 5,522,800 A | 6/1996 | Crocker |
| 5,542,926 A | 8/1996 | Crocker |
| 5,562,640 A | 10/1996 | McCabe et al. ............ 604/280 |
| 5,569,198 A | 10/1996 | Racchini |
| 5,571,089 A | 11/1996 | Crocker |
| 5,783,793 A | 7/1998 | Emerton et al. |
| 5,800,392 A | 9/1998 | Racchini |
| 5,906,502 A | 5/1999 | Fasano |
| 5,941,868 A | 8/1999 | Kaplan et al. |
| 5,961,483 A | 10/1999 | Sage et al. |
| 5,964,223 A | 10/1999 | Baran |
| 5,964,705 A | 10/1999 | Truwit et al. |
| 5,983,130 A | 11/1999 | Phipps et al. |
| 5,988,211 A | 11/1999 | Cornell |
| 5,997,527 A | 12/1999 | Gumucio et al. |
| 6,007,518 A | 12/1999 | Kriesel et al. |
| 6,017,318 A | 1/2000 | Gauthier et al. |
| 6,026,316 A | 2/2000 | Kucharczyk et al. ....... 600/420 |
| 6,029,083 A | 2/2000 | Flower et al. |

* cited by examiner

*Fig. 6*

DRUG DELIVERY AND CATHETER SYSTEMS, APPARATUS AND PROCESSES

BACKGROUND OF THE INVENTION

1. Field of the Invention

It has long been common practice for practitioners using a medical device to customize it on site. For example, practitioners may take a straight-ended catheter from stock and reshape it with the fingers, to achieve greater efficacy in a particular task. The present invention relates to a class of devices supplemented by computer supported designed-in variability, so that the user can make choices more accurately aimed at successfully accomplishing particular results.

The present invention relates to the field of delivery of materials into a patient, particularly at local sites within a patient using externally delivered devices to carry the materials to the desired site. The invention also relates to systems and processes for material delivery (especially pharmacologically active, view enhancing active or treatment active materials) to patients under Magnetic Resonance Imaging procedures.

2. Background of the Art

It is increasingly common and even necessary to administer a drug or other desired material to a carefully targeted part of the body. Currently such material is most often a solution or suspension of molecules, but in the future may include a suspension of nanoscopic devices. This targeted delivery is in contrast to conventional delivery methods where a drug is inserted into the bloodstream and treatment relies upon some of the drug finding the appropriate target. Targeted delivery has multiple advantages, when it can be done effectively. Much less of the drug is needed, which represents a double gain. Many drugs are costly, so the delivery of drugs in amounts greater than are needed for treating a specific area of a patient is wasteful and expensive. It is rare that any drug is wholly without negative effects (e.g., side effects, with reference to the desired result of the primary drug). In some instances, these adverse side effects arise only where the drug reaches a specific tissue. Therefore, restricting the drug to a target that does not include tissue that can be damaged avoids side effects completely. Even where that degree of precision in delivery is not possible, the side effects may be far more acceptable if limited to a small region around the target, with reduced impact on the body at large, while delivering the desired result on the target tissue at full strength. Even where the side effects are not directly life-threatening, it can be important to avoid them. For example, it is desirable to keep cancer chemotherapy drugs from the sites where they cause nausea and hair loss. That practice would be good both for patient morale and for patient persistence in taking the drug.

Some drug therapies use very strong or even toxic materials in the treatment, and even cryogenic treatments can cause collateral damage as the cryogenic material contacts non-targeted tissue. Hormonal treatments, where picogram delivery volumes are used because of the strength or activity of the material delivered and/or the limited area of treatment desired, can cause significant collateral damage when inappropriately delivered. This is particularly true in intraparenchymal procedures and other intracranial procedures where collateral damage, even on a small physical scale, can be very serious.

The majority of directed drug delivery systems tend to be essentially universal systems (intravenous or oral), indiscriminate local application (transdermal), or indiscriminate quasi-local (infusion from a catheter). Even the most advanced designs for MRI observable drug delivery as disclosed in U.S. Pat. Nos. 6,026,316; and 5,964,705 can only properly position the catheter, but do not provide specific structures that can adjust the rate and position of drug delivery from the catheter other than by standard fluid pressure control. Many different functions and controls are desirable in drug delivery systems, particularly with respect to the rate and direction of drug delivery. It would be a poor operational protocol to require essentially random direction positioning on a catheter of delivery outlets for a drug, cell culture, nanoscopic devices or other material, or require increased volumetric delivery, solely because the catheter could not be positioned with the outlets in an optimized position for desired delivery.

There are many different forms of drug delivery rate controls used in the medical field, both with intravenous, transdermal, and other forms of delivery. For example, U.S. Pat. No. 6,029,083 describes a "fail-safe" iontophoretic drug delivery apparatus and a corresponding method is provided. The apparatus includes a current generating circuit for sending a current through a patch, error detection circuitry, and a control circuit. The control circuit controls the current generating circuit. When errors are detected in the apparatus, the control circuit stops the current and disables itself.

U.S. Pat. No. 6,017,318 describes a feedback controlled drug delivery system that includes the automated sampling and analysis of a patient sample and dosing the patient based on the analysis. Automated sampling may be performed by direct analysis of the patient sample, such as for the measurement of a blood sample coagulation state or a glucose level. The drug delivery system includes a sample set that has a bidirectional patient tube that allows for delivery of the patient sample to an analyzer, and at another time, the infusion of a therapeutic drug. A controller receives a measurement from the analyzer, and based on that measurement, adjusts the delivery of the therapeutic fluid. The sample set has a quick-clear Leur fitting that allows for more effectively clearing a first fluid from a Leur fitting when starting a second fluid. The system also has a reagent cassette holder that protects, using a foam gasket, a reagent on a sample slide. Further, the system provides an interlock apparatus that assures a sample tube is occluded by either or both a slide clamp and by a platen arm compressing the sample tube to a peristaltic pump.

U.S. Pat. No. 6,007,518 describes a fluid delivery apparatus comprising:

(a) a fluid delivery assembly having an outlet for delivering fluid from the apparatus, said fluid delivery assembly including:
  (i) a base;
  (ii) means defining a conformable ullage overlaying said base for forming in conjunction therewith a reservoir having an outlet in communication with said outlet of said fluid delivery assembly;
  (iii) a cover assembly connected to said base, one of said cover assembly and said base having a receiving chamber interconnected with said reservoir; and
  (iv) a stored energy means for exerting forces on said means defining a conformable ullage, said stored energy means comprising at least one distensible membrane superimposed over said means defining a conformable ullage, said membrane being distensible by forces imparted thereon by said means defining a conformable ullage in response to fluids introduced into said reservoir, said forces establishing internal stresses within said distensible membrane, said stresses tending to return said distensible membrane toward a less distended configuration, said distensible membrane being generally conformable to the shape of said means defining a conformable ullage as said membrane is being distended thereby and also being generally conformable to the shape of said means defining a conformable ullage as said distensible membrane tends to return to said less distended configuration; and (b) a fill assembly interconnected with said fluid delivery assembly for filling said reservoir.

U.S. Pat. No. 5,997,527 describes a delivery device having a first chamber containing an osmotic agent, a membrane forming a wall of the first chamber through which fluid is imbibed by osmosis, a second chamber containing a beneficial agent to be delivered, and a moveable piston separating the two chambers. In fluid communication with the second chamber is an orifice which comprises a slit valve. In the presence of pressure, the beneficial agent pushes through the slit, opening up a channel for delivery of the beneficial agent and creating flow. Because the slit remains closed in the absence of flow (or when the pressure is below the pressure required to open the slit), back diffusion of external fluids is eliminated when the slit is closed, which prevents contamination of the beneficial agent in the second chamber by external fluids. In addition, forward diffusion of the beneficial agent out of the capsule is prevented when the slit is closed. The slit valve opens only to the minimum dimension required to allow the flow generated by the osmotic pumping rate. The slit valve also allows a flow path to open around any obstruction in the slit valve to prevent clogging.

U.S. Pat. No. 5,988,211 describes a method and apparatus for control of flow through an I.V. system, not a catheterized delivery system. That I.V. system comprises an I.V. Flow Controller incorporating an adjustable, differential pressure regulator that provides a constant but adjustable differential pressure across a fixed orifice. One end of the adjustment range provides shut-off and the other end full-flow. The adjustment range covers flow rates from zero to 250 ml/hr. At a given setting, the flow rate is independent of the total hydrostatic head height between the supply reservoir and a patient, provided the head height is greater than the pressure drop across the orifice at the maximum regulated flow rate, plus venous pressure, plus the pressure drop in the indwelling catheter.

U.S. Pat. No. 5,983,130 describes an electrically controlled delivery system comprising an electrotransport agent delivery device for delivering a therapeutic agent through a body surface, and a method for increasing agent delivery efficiency, is provided. The device includes a current controller which delivers a pulsating electrotransport current and peak current density $I_{max}$, $I_{max}$ being greater than a critical current density level $I_c$ above which the body exhibits a non-transitory higher agent delivery efficiency. Methods for increasing electrotransport delivery efficiency (E) of an agent through a body surface by creation of a higher agent delivery efficiency state are also provided.

U.S. Pat. No. 5,964,223 describes a method and apparatus for delivering a medicine to a patient via the patient's respiratory system with control and efficiency. A nebulization catheter is positioned in the patient's respiratory system so that a distal end of the nebulization catheter is in the respiratory system and a proximal end is outside the body. In a first aspect, the nebulization catheter may be used in conjunction with an endotracheal tube and preferably is removable from the endotracheal tube. The nebulization catheter conveys medicine in liquid form to the distal end at which location the medicine is nebulized by a pressurized gas or other nebulizing mechanism. The nebulized medicine is conveyed to the patient's lungs by the patient's respiration which may be assisted by a ventilator. By producing the aerosol of the liquid medicine at a location inside the patient's respiratory system, the nebulizing catheter provides for increased efficiency and control of the dosage of medicine being delivered. In further aspects of the nebulizing catheter apparatus and method, alternative tip constructions, flow pulsation patterns, centering devices, sensing devices, and aspiration features afford greater efficiency and control of aerosolized medicine dosage delivery.

U.S. Pat. No. 5,961,483 describes novel methods and devices for iontophoretically administering therapeutic doses of cell adhesion receptor antagonists in a controlled manner through the skin. Such antagonist compounds include but are not limited to antagonists of the IIb/IIIa and $α_vβ_3$ integrins and related cell surface adhesive protein receptors. The present invention includes iontophoretic delivery devices comprising cell adhesion receptor antagonists. Such methods and devices are useful, alone or in combination with other therapeutic agents, for the treatment of thromboembolic disorders, angiogenic disorders, inflammation, bone degradation, cancer metastasis, diabetic retinopathy, restenosis, macular degeneration, and other conditions mediated by cell adhesion and/or cell migration and/or angiogenesis.

U.S. Pat. No. 5,941,868 describes Angiogenesis in cardiac and other tissues being promoted by the transmural delivery of angiogenic factors such as VEGF, FGF, EGF, and PDGF, through blood vessels and other body lumens into the surrounding tissue. Usually, the angiogenic factor is delivered using a catheter having infusion parts at its distal end. Optionally, the distal end of the catheter is radially expanded to engage the infusion parts directly against the blood vessel wall. A variety of catheter systems useful for the direct transmural infusion of angiogenic factors into the blood vessel wall are also well-described in the patent literature. Most commonly, balloon catheters having expandable distal ends capable of engaging the inner wall of a blood vessel and infusing an angiogenic factor directly therein are well-described in the patent literature. See, for example, U.S. Pat. Nos. 5,318,531; 5,304,121; 5,295,962; 5,286,254; 5,254,089; 5,213,576; 5,197,946; 5,087,244; 5,049,132; 5,021,044; 4,994,033; and 4,824,436. Catheters having spaced-apart or helical balloons for expansion within the lumen of a blood vessel and delivery of a therapeutic agent to the resulting isolated treatment site are described in U.S. Pat. Nos. 5,279,546; 5,226,888; 5,181,911; 4,824,436; and 4,636,195. A particular drug delivery catheter is commercially available under the trade name Dispatch™ from SciMed Life Systems, Inc., Maple Grove, Minn. Non-balloon drug deliver catheters are described in U.S. Pat. Nos. 5,180,366; 5,112,305; and 5,021,044; and PCT Publication WO 92/11890. Ultrasonically assisted drug delivery catheters (phonophoresis devices) are described in U.S. Pat. Nos. 5,362,309; 5,318,014; and 5,315,998. Other iontophoresis and phonophoresis drug delivery catheters are described in U.S. Pat. Nos. 5,304,120; 5,282,785; and 5,267,985. Finally, sleeve catheters having drug delivery lumens intended for use in combination with conventional angioplasty balloon catheters are described in U.S. Pat. Nos. 5,364,356 and 5,336,178.

U.S. Pat. No. 5906,502 describes an apparatus for accurately infusing fluids into a patient at specific rates over an extended period of time and the method for making same. The apparatus includes one or more dispensers of a low profile, laminate or layered construction each having a stored energy source in the form of a distensible membrane or an elastomeric cellular mass, which in cooperation with the base, defined a fluid chamber having a fluid inlet and a fluid outlet. The apparatus further includes, in lieu of a rigid ullage, a high novel, conformable ullage made of yieldable materials. The conformable ullage uniquely conforms to the shape of elastomeric membrane as the membrane returns to its less distended configuration. This arrangement will satisfy even the most stringent delivery tolerance requirements and will elegantly overcome the limitations of materials selection encountered in devices embodying the rigid ullage construction. Additionally, with the novel ullage construction, the ullage can be located either between the base and the fluid to be delivered, or alternatively, can be located between the elastomeric membrane and the fluid to be delivered. Further, a plurality of sub-reservoirs can be associated with a single ullage thereby making it possible to incorporate a wide variety of delivery profiles within a single device.

U.S. Pat. Nos. 5,571,089; 5,542,926; and 5,522,800 describe a Low Profile Perfusion Catheter, for use in coronary angioplasty applications. Preferably, the catheter is provided with an inflatable dilatation balloon, and a perfusion lumen extending therethrough. The diameter of the perfusion lumen is enlargeable from a first, reduced diameter to a second, enlarged diameter. In one embodiment, an axially movable tubular support is movable within the lumen from a proximal, insertion position to a distal perfusion position. In another embodiment, the support is radially expandable. In a further embodiment, a porous drug delivery balloon is provided.

U.S. Pat. No. 5,385,547 describes a drug delivery device for coupling a first container including a beneficial agent to a second member. In an embodiment, the device includes a substantially hollow member having a cannula mounted within a wall that divides the substantially hollow member into a first and second section. The first section includes means for receiving at least a portion of a first container. The substantially hollow member includes a wall that defines an exterior of the first section that is substantially flexible. A number of different cannula and flow path structures within the hollow member are possible.

U.S. Pat. No. 5,498,236 describes a catheter suitable for introduction into a tubular tissue for dissolving blockages in such tissue. The catheter is particularly useful for removing thrombi within blood vessels. In accordance with the preferred embodiments, a combination of vibrating motion and injection of a lysing agent is utilized to break up blockages in vessels. The vessels may be veins, arteries, ducts, intestines, or any lumen within the body that may become blocked from the material that flows through it. As a particular example, dissolution of vascular thrombi is facilitated by advancing a catheter through the occluded vessel, the catheter causing a vibrating stirring action in and around the thrombus usually in combination with the dispensing of a thrombolytic agent such as urokinase into the thrombus. The catheter has an inflatable or expandable member near the distal tip which, when inflated or expanded, prevents the passage of dislodged thrombus around the catheter. The dislodged portions of thrombus are directed through a perfusion channel in the catheter, where they are removed by filtration means housed within the perfusion channel before the blood exits the tip of the catheter. Catheters that allow both low frequency (1–1000 Hz) vibratory motion and delivery of such agents to a blockage and a method for using such catheters are disclosed.

U.S. Pat. Nos. 5,800,392 and 5,569,198 describe an apparatus for delivering an agent to a treatment area. The apparatus includes a catheter that has a distal portion and a proximal portion. The catheter defines a lumen. A pressure regulator is in fluid communication with the lumen. A selectively inflatable member is also in fluid communication with the lumen, and is formed from a membrane. The membrane has first and second portions. The first portion defines pores sized from about $0.05\ \mu$ to about $1\ \mu$ and has a pore density from about $10^6$ pores/cm$^2$ to about $10^9$ pores/cm$^2$. The flux rate is from about 0.001 ml/(min-cm$^2$-atm) to about 0.4 ml/(min-cm$^2$-atm). The second portion is substantially impermeable.

U.S. Pat. No. 5,783,793 describes a laser drilling process capable of producing a plurality of holes in a pharmaceutical dosage form at high speed. The process utilizes a high power $CO_2$ laser steered by an acousto-optic deflector together with various mirrors and optical components to achieve the correct beam path geometry, in order to produce an unlimited number of holes through the surface or coating of a dosage form, at rates up to 100,000 units or more per hour.

Even though restricted area targeting is highly desirable from a medical standpoint, this type of procedure adds to the traditional complexity of computing dosage and delivery rates. Instead of a single figure of blood concentration, controlled by the rates at which the drug enters and at which it diffuses, flows and is absorbed, metabolized or excreted by various tissues, concentration becomes a distinct time-varying number at each part of the body. Since the effects of a drug vary in complex ways on concentration (scopolamine, for example, is an anti-nausea drug in a narrow range of levels, neither too high nor too low), its administration must ensure that the concentration at the target tissue is correct for the desired effect. At the same time, the concentration at other points must minimize undesired effects (often, but not always, by minimizing concentration at such points). Planning treatments and procedures thus requires prediction and flexibility of drug (or material) delivery.

Prediction at real-time speed of drug transport is becoming possible due to improvements in computing machinery and in methodology (see the commonly assigned copending patent application of R. Raghavan et al., "A Method and Apparatus for Targeting Material Delivery to Tissue", SLWK docket no. 723.032US1 and also the journal article by Paul Morrison et al., "High-flow microinfusion: tissue penetration and pharmacodynamics", American Journal of Physiology 266, p. R292–R305, 1994). This type of procedure permits planning not only of the timing and quantity of active material to be administered, but enables customized design of the form of the administering device for the best possible effect. The present invention provides designs for improved delivery systems that assist in improving the ability of the practitioner to implement the planned procedure.

Given scan data (magnetic resonance, CAT, etc.) on the anatomy and physiology of a patient, and in some cases on the transport of labeled materials in 'scout' injections, one can construct a numerical model of transport which permits prediction of the evolving concentration level of the material to be administered.

Such prediction requires a model of the transport process in tissue, as described in the above identified copending patent application "A Method and Apparatus for Targeting Material Delivery to Tissue". It also requires boundary conditions that specify the pressure or flow rate of fluid at sufficient distance from the injection device, and at the place(s) where the fluid leaves the device and enters the tissue.

BRIEF SUMMARY OF THE INVENTION

The present invention defines a class of customizable injection devices or delivery instruments whose basic form is a stiff tube with holes of user-selectable size at several user-selectable places, whose use includes a method of selection and construction of a particular device from such a class of devices for a particular treatment procedure using computer-assisted means. Thus, the user may make selections among the available choices (such as selection of hole size, selection of hole location, etc.), and a method can be practiced for making such user-selection serve the goals of delivery of materials such as drugs, cells, or of devices sufficiently small and numerous to be delivered in fluid suspension. The tube is relatively stiff in the sense that it deflects by an amount between 0° and 15° under the stresses of insertion and placement at the end of a catheter, and varies less than 5 or less than 10% per cent in cross-sectional area when so deflected to the maximum of about 15 degrees.

The selection method may be practiced as follows. The user selects target tissues where the presence of the material is desired, and selects maximum and minimum target concentrations, and identifies tissues vulnerable to the material to be introduced, with maximum permitted concentrations identified in the region of the vulnerable tissues. This target information may be retained in the user's consciousness, or input to the machine by use of an interface, such as a visual interface (e.g., with pre-procedure image information or real-time image information). The user may then specify a hole pattern (e.g., a number of holes, a distribution of holes, the size of holes, the position of holes, etc.), and see the predicted result with a selected time course of imposed pressure (or imposed flow rate) of the material at a specified concentration in injected fluid. Alternatively, e.g., if the desired concentration criteria have been communicated to a computer, the user may request the system to explore different patterns (as defined above) and injection plans to produce a result satisfying the input criteria, or coming as close to such satisfaction as is acceptable or possible.

BRIEF DESCRIPTION OF THE DRAWINGS

Drawing 1. A tube tip with holes in various positions and dimensions, and membranes of various thicknesses between them.

Drawing 2. A tube tip with holes in various positions and dimensions, arranged by revolving collars over holes created in manufacture.

Drawing 3. A tube tip with holes in various positions and dimensions, created by assembling cylindrical units with holes and membranes of different sizes.

Drawing 4. A ramrod device for placing permeable barriers in a tube at pre-planned positions.

Drawing 5. Concentrations of a diffusing material around a multi-hole catheter.

Drawing 6. A field of coefficients (here represented by a single number at each point, with a 2D grid standing for three dimensions) governing the transport of injected material.

Drawing 7. The flow chart of the computation and interaction procedure of the invention.

DETAILED DESCRIPTION OF THE INVENTION

Delivery Instrument

Figure 1:
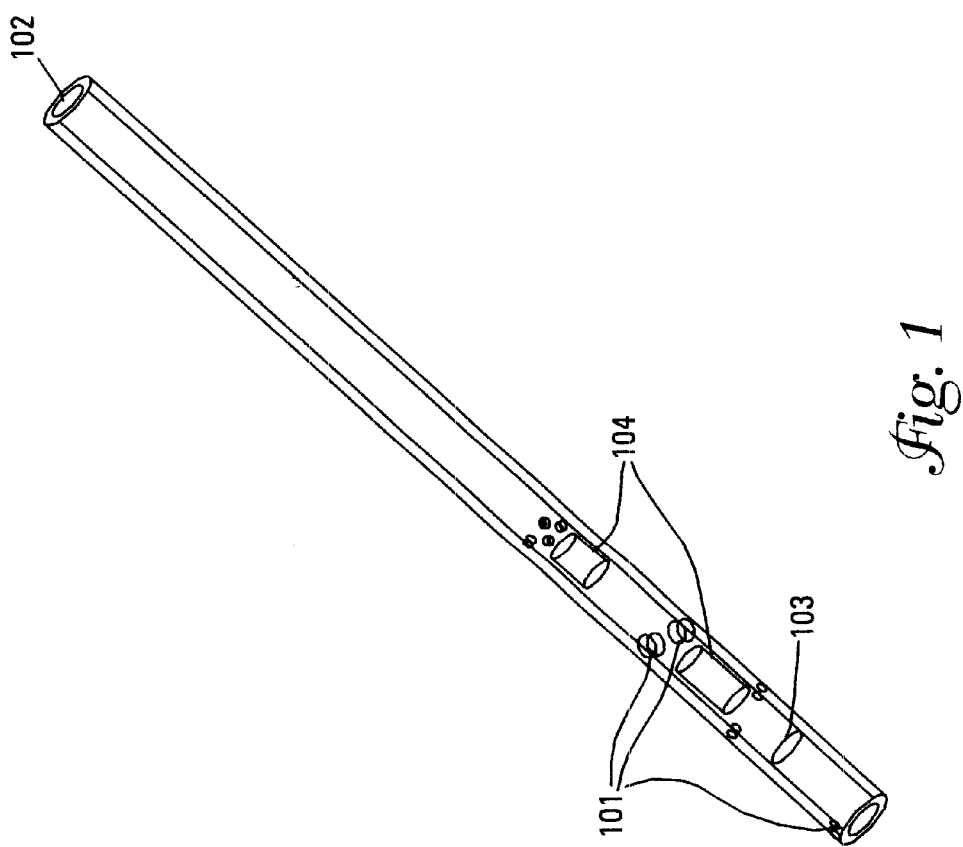
Figure 2:
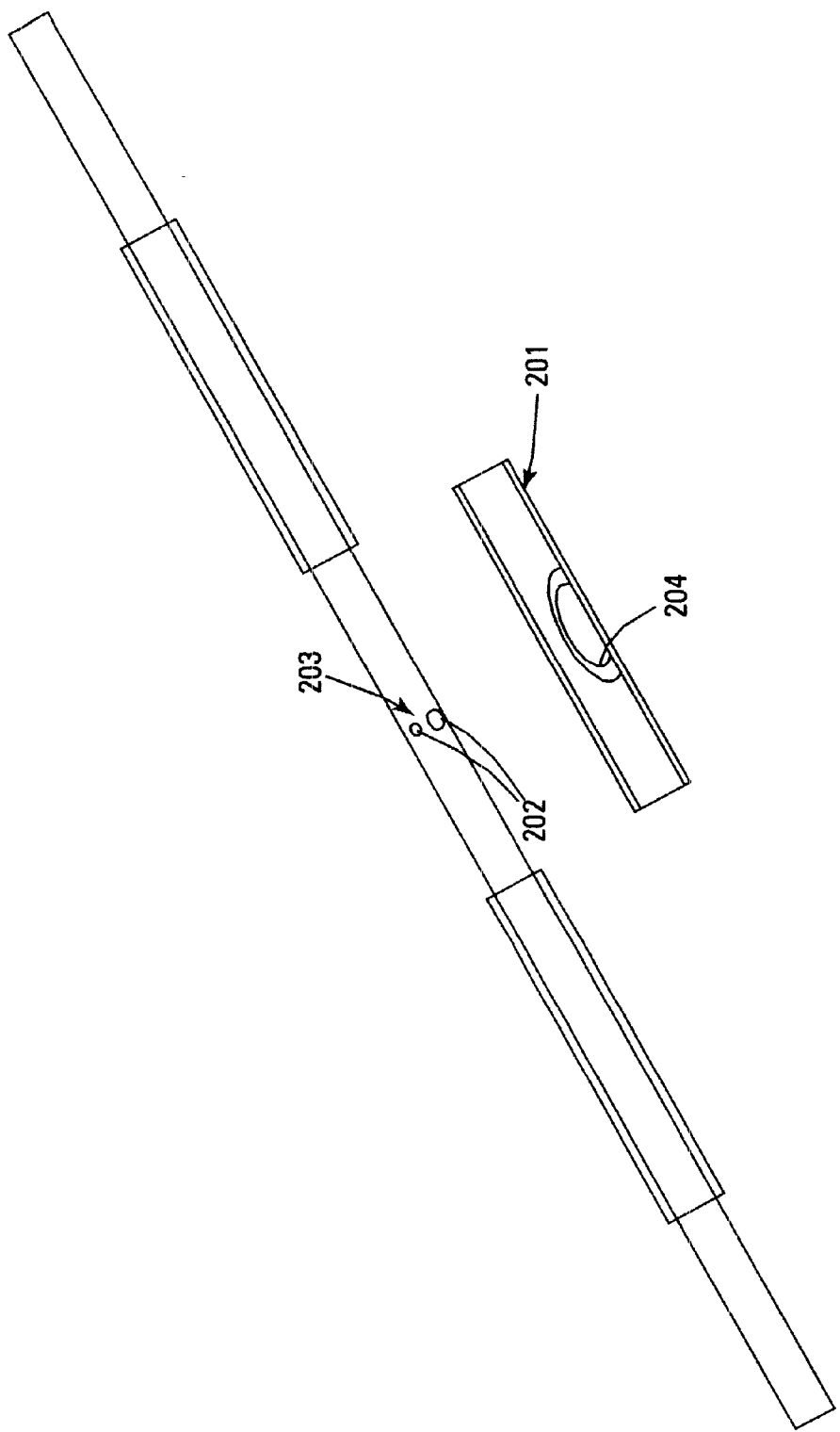
Figure 3:
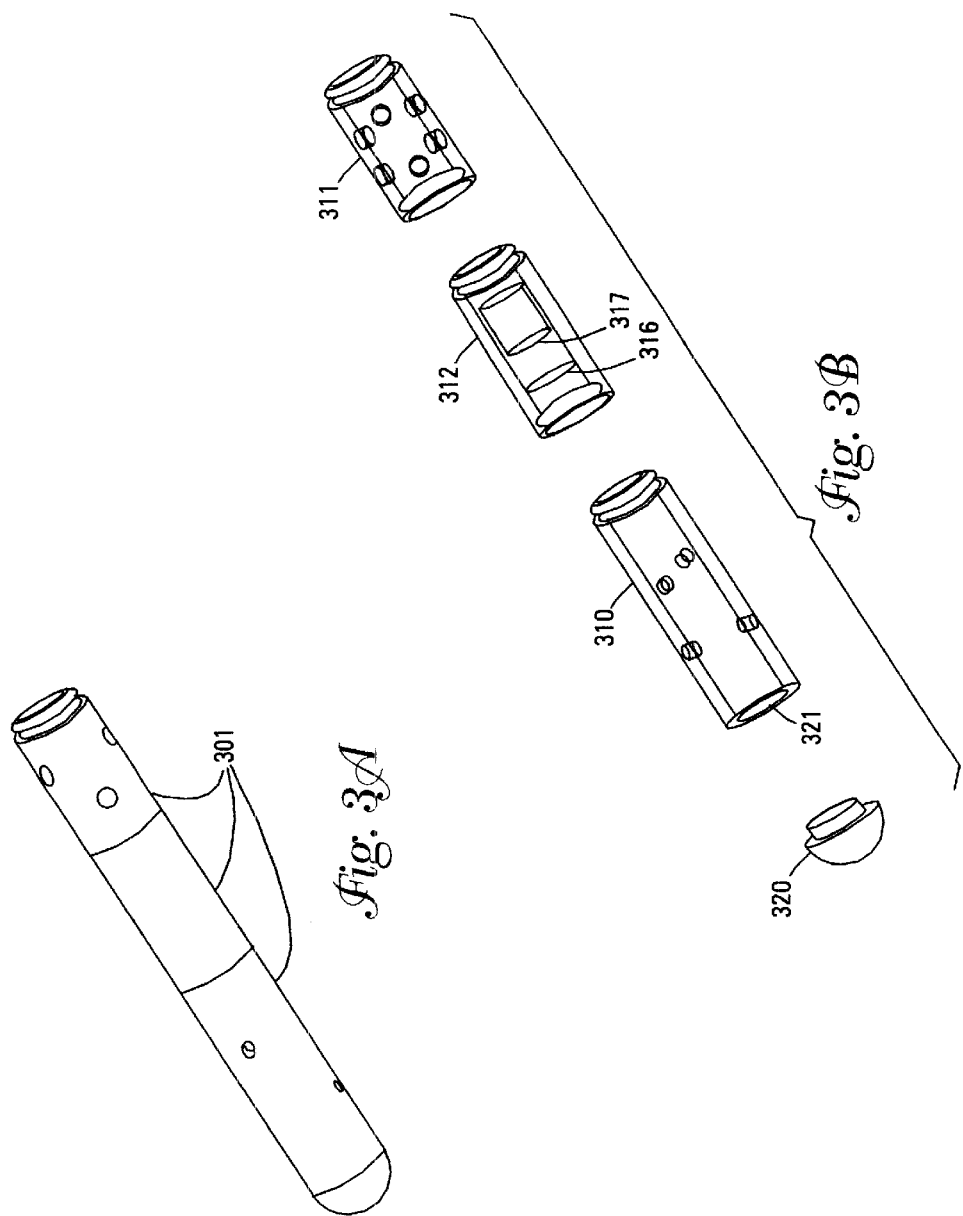
Figure 4:
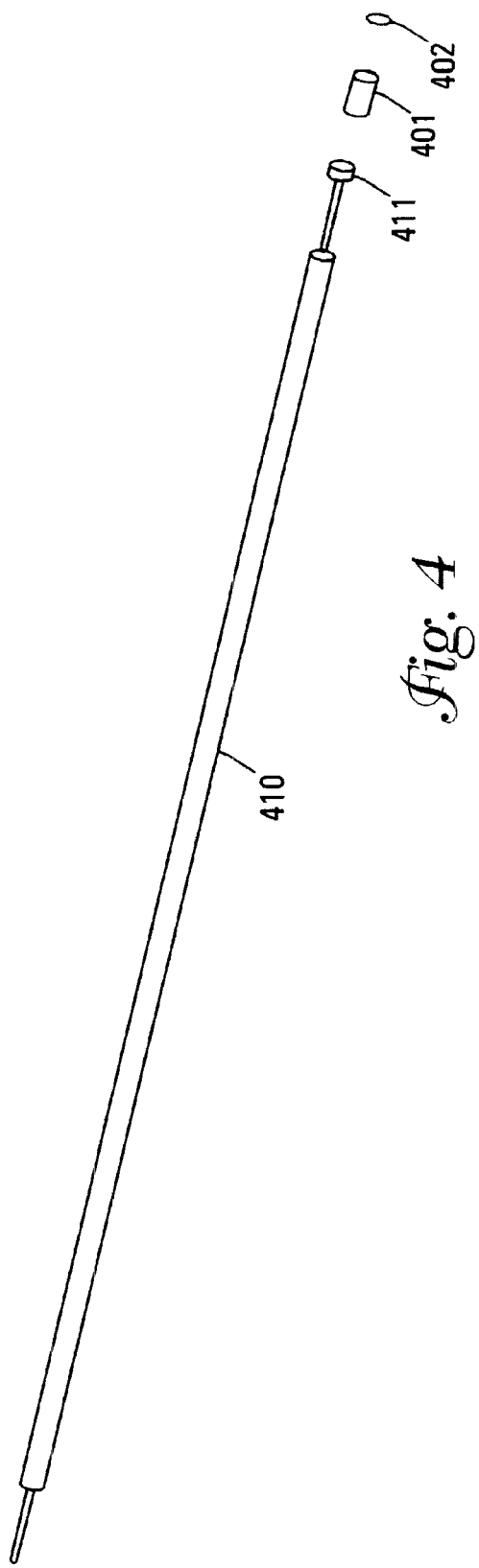
Figure 5:
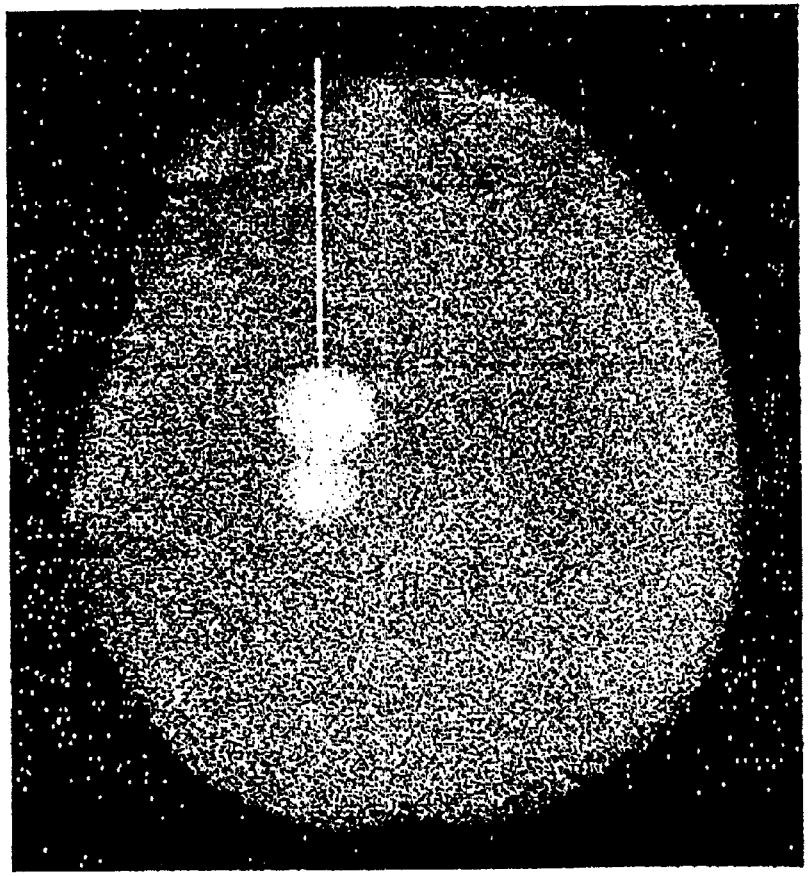
Figure 7:
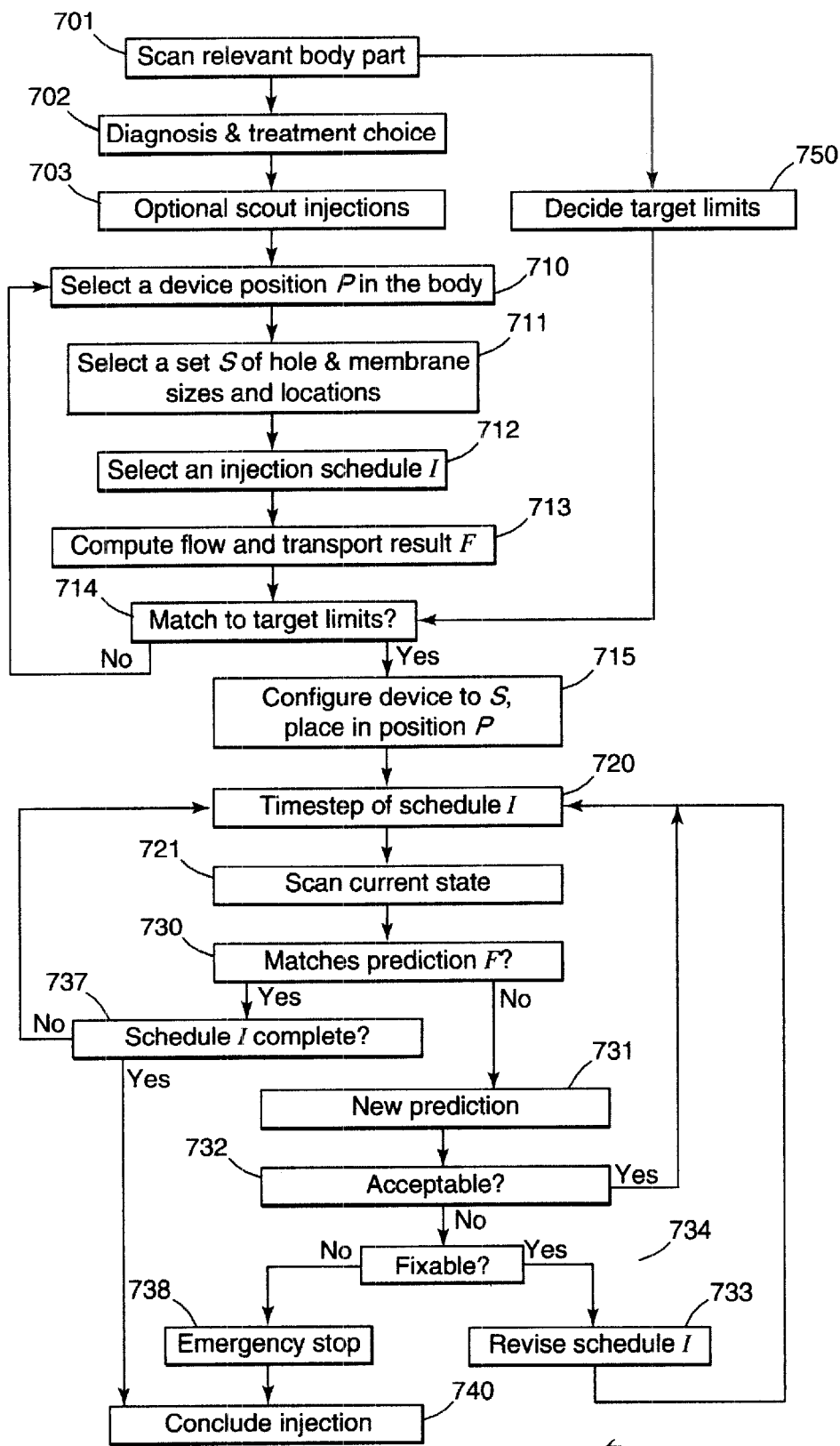

The physical component or device of the present invention is a tube (Drawing 1), rigid or sufficiently stiff to retain its internal cross-section (with a reduction not to exceed 10% and preferably equal to or less than 7% or 5%) when bent through a deflection of up to 15°, and deflecting by at most this amount under the stresses usual for an inserted catheter. The limitation on the change in cross-section is of significance because flexing of the device will often occur during procedures. If the cross-section alters, that would introduce a variation in device performance that would complicate the implementation of controls, as the flow and delivery rate properties of the device would change without intent. This tube is pre-engineered with holes 101 of adjustable sizes and positions, or capable of being drilled with holes of chosen sizes and positions. The tube may be mounted on a rigid or flexible channel 102 through which fluid containing dissolved or suspended material capable of moving through or onto bodily tissue may be transmitted to the interior of said tube. That material then passes through said holes to contact the tissue. Within said tube may be placed one or more control mechanisms that can regulate the passage of material through the holes. Regulation includes all rates between complete blockage of material through the hole to allowing free passage of material through the hole. Such regulation and control mechanisms may be mechanical, electromechanical, or quasi-mechanical in nature. A purely mechanical control mechanism would be a slidable or rotatable cap that would obscure some holes, all holes, or portions of holes. For example, with a top of the element having twenty holes for release of material, there could be a cap with fifty holes distributed thereon. Rotation of the cap through ninety, one hundred twenty, one hundred sixty, one hundred eighty, or up to three hundred and sixty degrees would expose various portions or numbers of the twenty holes. For example, at a position defined as zero degree rotation, zero holes might be exposed (that is all twenty holes would be covered, preventing material delivery). At a five degree rotation, 1–3 holes at a specific position relative to the device would be exposed to allow delivery of material from those exposed holes. At a ten degree rotation, 3–5 holes at specific positions relative to the exterior of the device would be exposed. At a fifteen degree rotation, 5–8 holes at specific positions would be exposed to release material. At a twenty degree rotation, 9–12 holes would be exposed. At a thirty degree rotation, 12–15 holes would be exposed at specific positions on the outside of the device. At a forty-five degree rotation, 15–18 holes would be exposed, and at a sixty degree rotation, 18–20 holes would be exposed. With further degrees of rotation (or with intermediate degrees of rotation), different numbers of holes would be exposed (or more covered), and the position or relative location of those holes could be changed. For example, the first forty five degrees of rotation could expose holes in one cross-section quadrant of the device, the next forty-five degrees expose holes in another cross-section quadrant of the device, and so forth, with all four quadrants being individually or collectively exposed. In this manner, if the visualization of the delivery of the drug or material from the device (as taught in U.S. Pat. No. 6,026,316) shows that the alignment of the device (e.g., a catheter) is delivering material too broadly (radially at all points along the tube surface) or in a quadrant facing away from the target tissue), the device may be remotely controlled by this mechanical control to redirect the output of material more closely towards the target tissue. Mechanical control could be effected by manipulation or mechanical control of a guidewire attached to the cap. Electromechanical control could employ electronically remote controlled servos or robotics that move caps, covers or the like around holes in the surface of the device. Micromotors could shift one or more hole-covering or hole-blocking elements to increase or decrease the rate of flow of material and the direction of flow of material from the device. A quasimechanical system would include resistively heated sections where flow would increase because of thermal expansion around or by holes; remotely initiated elastic deformation of caps to adjust the size of holes, and the like. Membranes may also be used that are electrically or thermally or elastically responsive to adjust flow rates through them. For example, in FIG. 1, membranes 103 or blocks 104 of permeable material separate the holes, modifying the transmission characteristics of the fluid between them.

The fabrication of the instrument may use any of a number of methods familiar to those skilled in the art. A wide selection of options may be pre-manufactured, saving on-site time at the expense of increased stock and storage costs. The preferred embodiment of the present invention is local customization, whereby the holes may be made or adjusted by the use of local equipment acting on a small set of standard parts, by various methods. Those described here are selected precisely for their suitability to on-the-spot fabrication of the instrument, rather than requiring factory production facitilies. For instance, as noted earlier, the adjustability of the holes may be achieved in several ways. In one implementation, a plain tube is inserted in a jig and holes drilled into it with conical drill bits, so that the depth controls the hole diameter. Evidently this function can be performed by a small automated system, but equally a plan of the holes could be printed out on adhesive paper. The user would attach this printed hole distribution map to the tube, and drill the holes by hand, extending the current practice of radiologists in adjusting the active end of a catheter. Alternatively, the distribution of holes could be imaged on a photolithographic resist layer and the image developed and etched to produce the appropriate hole distribution.

Alternatively, and mentioned here for purposes of illustration only, the tube may be manufactured with a closely spaced sequence of cylindrical collars (Drawing 2, in an exploded view). Under each collar 201 the tube is ringed with holes 202, alternating with regions 203 of un-pierced tube. Each collar has a single hole 204, which may be aligned partially or completely with any one of the holes, enabling the user to create a hole of varying cross-section in any one of a set of positions around the tube. To avoid unplanned leakage this requires precise engineering of a throwaway item, and is thus well suited to profitable medical engineering.

The tube may also be assembled (Drawing 3) by sticking together short cylindrical segments 301 from a stock 310 of such pieces, with holes 311 and without holes 312, of varying lengths. In this implementation, some of the pieces 312 may contain permeable membranes 316 or blocks 317 whose permeability is marked on the outside, so that these may be added by the same assembly process. An optional cap 320 would allow the user to block the hole 321 at the end. If joining of the segments is performed by a heat-welding system in which one part must pass down the lumen of the combined tube, which would be blocked by the inclusion of permeable membranes, such membranes may be added later, as described in the discussion of Drawing 4.

Holes may be photolithographically etched, laser etched, chemically milled, electrical discharge milled (EDM), or mechanically milled by other available procedures.

Where the tube is supplied as an unbroken cylinder rather than as pieces, Drawing 4 shows how permeable or discontinuously permeable slidable elements (permeable cylindrical blocks 201 or membranes 202) capable of lodging in the interior may be pushed down the tube to the required depth, using a calibrated ramrod 410 whose tip 411 pushes an element inside the tube. Again, by redesigning the distribution of holes and selecting appropriate hole patterns in the slidable elements, the direction and rate of the material release can be controlled with significant specificity.

In each design approach, it is often appropriate to include elements (e.g., MR markers or MR responsive markers) that make the orientation of the tube visible to the imaging system in use, as twisting the tube turns side holes to face different parts of the tissue. In certain cases, the resulting change in concentration distribution can be significant.

Pressures in the Tube

Given the pressures or the flow rates at the holes, and their cross-sections, the methods described in commonly assigned copending application in the name of R. Raghavan et al., and titled "A Method and Apparatus for Targeting Material Delivery to Tissue", which disclosure is incorporated herein in its entirety, serve to compute the resulting transport of material through tissue.

These pressures and flow rates are the result of interaction among the tube, the surrounding tissue and the fluid already present, but to a certain approximation they may be computed for the tube on the assumption of a fixed background pressure in the surrounding tissue. Specifically, let us number the holes according to their distance from the inlet end. If more than one port(s) has the same distance from the inlet end, then the more than one port(s) is or are mathematically replaced by a single port with a cross-section area equal to the total cross-section area of all such ports. (For the interior of the tube, the results are equivalent.)

Now, let

A=Area of cross section of the catheter
V=Velocity of fluid infusion
$P_a$=Ambient pressure
K=Hydraulic permeability of the catheter
L=Length of the catheter
t=Thickness of the catheter wall
η=Coefficient of viscosity of the fluid
$L_i$=Distance between port i and (i-1)
$α_i$=Cross sectional area of port i
$κ_i$=Tissue hydraulic permeability at port i
$q_i$=Velocity of fluid outflow at port i
$v_i$=Velocity of fluid flow at port i along the catheter
$p_i$=Pressure at port i
N=Total number of ports (including the outlet port)

We ignore possible variability of the hydraulic permeability along the length of the catheter and use the value $(R^2/8)$ that is appropriate for steady Poiseuille flow in a tube with circular cross section of radius in case we are modeling viscous laminar flow. In the porous medium, Darcy's law relates fluid velocity to the pressure gradient and we may use this to express the outflow velocity at a port in terms of the pressure gradient across the port. So the fluid velocity $v_i$ at port i along the catheter is $$v_i = -\frac{K}{\eta}\nabla p = -\frac{K}{\eta}\frac{(p_{i+1} - p_i)}{L_{i+1}} \tag{1}$$

whereas the velocity of fluid outflow $q_i$ at port i is $$q_i = -\frac{\kappa_i}{\eta}\nabla p = -\frac{\kappa_i}{\eta}\frac{(p_a - p_i)}{t} \tag{2}$$

The fluid is assumed incompressible. Therefore the total fluid volume flow must equal the total fluid volume inflow minus the fluid flow through all the previous ports. At any arbitrary port i except the outlet end, we may write $$v_i A = VA - \sum_{j \leq i} q_j a_j \tag{3}$$

or $$\frac{K}{L_{i+1}}(p_i - p_{i+1}) = V\eta + \sum_{j \leq i} \frac{\kappa_j a_j}{tA}(p_a - p_j) \tag{4}$$

and at the outlet end, we have the flux conservation equation $$\sum_{j=1}^{N} \frac{\kappa_j a_j}{tA}(p_a - p_j) = V\eta \tag{5}$$

This set of (N+1) equations can be represented in matrix form as $$B\begin{pmatrix} p_0 \\ p_1 \\ \vdots \\ p_N \end{pmatrix} = V\eta \begin{pmatrix} 1 \\ 1 \\ \vdots \\ 1 \end{pmatrix} - C\begin{pmatrix} p_0 - p_a \\ p_1 - p_a \\ \vdots \\ p_N - p_a \end{pmatrix} \tag{6}$$

with $$B = \begin{pmatrix} \frac{K}{L_1} & -\frac{K}{L_1} & & & & & \\ & \frac{K}{L_2} & -\frac{K}{L_2} & & & & \\ & & \cdots & \cdots & & & \\ & & & \cdots & \cdots & & \\ & & & & \cdots & \cdots & \\ & & & & & \frac{K}{L_N} & -\frac{K}{L_N} \\ 0 & 0 & 0 & \cdots & \cdots & 0 & 0 \end{pmatrix} \tag{7}$$

and $$C = \frac{1}{tA}\begin{pmatrix} 0 & 0 & 0 & \cdots & \cdots & 0 \\ 0 & \kappa_1 a_1 & 0 & \cdots & \cdots & 0 \\ \cdots & \kappa_1 a_1 & \kappa_2 a_2 & 0 & \cdots & \cdots \\ \cdots & \cdots & \cdots & \cdots & \cdots & \cdots \\ \cdots & \cdots & \cdots & \cdots & \cdots & 0 \\ 0 & \kappa_1 a_1 & \kappa_2 a_2 & \cdots & \cdots & \kappa_N a_N \end{pmatrix}. \tag{8}$$

Solving equation (6) gives the pressure at all the ports, and at the inlet and outlet ends. Since only pressure differences influence the flow, we have to fix (specify) one of the pressures; it is convenient to fix the ambient pressure (possibly to zero, in which case all other pressures are measured with respect to the ambient pressure). These pressure values obtained from (6) can be plugged back in the Darcy equations to give fluid outflow velocities at the ports, and thereby the fluid volume flow.

Planning System

Given a customization system for specifying and fabricating tubes with a chosen spacing of holes and inter-hole membranes (with specified cross-sections and permeabilities), as above, and a means of computing the transport of injected material within tissue for conditions specified at the exit points in the injection instrument, such as that in the aforementioned "A Method and Apparatus for Targeting Material Delivery to Tissue", the user may select a particular instrument optimal for a given treatment. The user-selection element of the present invention may proceed as follows:

Image guidance permits a user injecting a material such as a drug solution or a suspension of cells or nanodevices, or any material that can flow and diffuse in the brain, to place a delivery instrument such as a catheter into (for example) a human brain, and see where it is located relative to scan-visible structures. In present practice, the user makes a plan for injection, determining the quantity of the material to be loaded into the delivery system, the pressure or flow rate (perhaps variable) at which the substance is to be injected, and the time over which the flow is to be maintained. The objective of such a plan is to deliver the substance in desired quantities in 'target' tissues, often while minimizing the amount delivered to non-target tissues (where it would be wasted) and to vulnerable tissues where the substance would do harm. It is also desirable to avoid excessive fluid pressure and to minimize the extent and duration of the resulting edema (swelling) of the tissue encountered by the material and the fluid carrying it. Commonly, this plan is entered into a computer which will control the injection process, but direct hand control is also possible. This plan is then followed, with a change only if visually inspected images (e.g., U.S. Pat. No. 6,026,316) of the diffusing material makes clear that concentration, pressure or edema is not following the course expected by the user. Since the evolving concentration, pressure and edema are 3D scalar fields in the midst of complex 3D structures, visual inspection requires a strong grasp of the 3D relationships revealed by scan data. Current 3D display techniques do not display these relationships clearly enough to guarantee fast comprehension and appropriately swift action by the medical user. It is rare that undesired consequences are seen fast enough to limit their scope.

The present invention replaces or augments such visual inspection by enabling the computer to enter this part of the control loop, with optimal planning of the tube outlets as well as of the injection schedule.

At a simple level of control in the present invention, the user specifies a position for placement of the device (as is now done), and also specifies magnitude, distribution and location of holes and membranes. The user then specifies an injection schedule (quantity, duration, pressure/flow-rate) to the computer. We refer to these combined specified features (a specification) as a plan. The computer then solves the transport problem on the assumption that this plan is followed, using the field of parameters established as in the above identified copending U.S. Patent Application "A Method and Apparatus for Targeting Material Delivery to Tissue", or otherwise, together with available subsidiary data such as background interstitial fluid pressure and blood pressure to specify boundary conditions. The system displays the predicted values of concentration, pressure and edema, and the user has the opportunity to examine them at non-crisis speed and determine whether they are satisfactory. If not, the user repeatedly changes the plan, until an acceptable result is predicted. At this point, the schedule is implemented under computer control.

At a more strongly supported level of control, the user modifies the hole and membrane distribution by the use of a graphical user interface and specifies target tissues by marking them (for example, by using a 2D or 3D mouse to click on points, specifying ball-shaped regions of adjustable radius; or, outlining a target region; or, moving a 2D or 3D mouse through an image of the region of interest and seeing a resulting spray-can-like superposed image showing the intensity of target values so input for corresponding points, etc. Minimum and maximum target concentrations may be input separately. Similarly, the user may mark vulnerable tissues, and quantify their vulnerability to excess concentration, pressure or edema. The user inputs a plan as above, and the computer predicts the resulting concentrations. In this mode, the computer display includes markers for agreement with the user's goals, so that visual inspection is guided to possible regions of concern. When a chosen plan is implemented, using scan-visibility of the injected substance the computer can monitor deviation from the expected time course of concentration, and detecting problems earlier (and thus more usefully) than visual monitoring. Where deviation beyond a threshold level is detected, the computer derives revised estimates for the transport parameters in the tissue and deduces revised predictions for the results of the plan. If these involve values pre-specified by the user as unacceptable, the computer may pause the injection for new user input.

At a higher level again, where the computer is capable of carrying out multiple predictive simulations of transport in available time, it may search the space of possible plans for the plan(s) with the result most quantitatively desirable according to the user-specified result. (For example, it may begin by heuristically choosing an initial plan, perhaps a standard one, and investigate the predicted result of successive changes in it, changing the current reference plan where it sees improved results. In general the physics will not allow exact achievement of a particular user-specified target concentration, pressure or edema, so this is not well posed as an inverse problem. The system's goal must be to find a plan whose results are within user-specified limits.) Such plan(s) may be presented to the user, to be accepted or rejected by key-strokes, mouse click, voice, or other input means devoid of quantitative detail; or, the user may quantitatively modify the plan(s), view the consequences of each modified plan, and select among this larger set.

Where the computer is thus capable of generating plans adjusted to user goals, when monitoring the real injection reveals a deviation from the expected concentration changes, the computer may not only deduce corrections to the assumed field of transport parameters, and create revised predictions and warn if the results are unacceptable, but the computer may find a revised plan with more satisfactory results and (subject to user approval, or autonomously) implement the revisions while the injection is in progress.

This variant of the invention requires the greatest speed, and is the most likely to require implementation with dedicated hardware optimized for the purpose of solving the necessary equations quickly.

Flow of the Method

In summary, Drawing 7 shows the logic of the present invention. First, the relevant target tissue or body part is scanned (701) using one or more 3D imaging modalities such as magnetic resonance imaging, CT, ultrasound, etc. From an analysis of the scan, a physician arrives at a diagnosis and decides on a treatment plan (702). A choice of target limits (desired or undesired drug levels in different areas) is made (750) based on the scan. Scout injections (703) may be used to track the transport of neutral agents, from which transport behavior of actual therapeutic agents may be deduced by appropriate scaling. Next, the physician makes a (virtual) selection (710) of device position within the body followed by selection (711) of a set of holes and membrane sizes and locations on the virtual device from which therapeutic agents are to be released. A choice of injection schedule is then made (712). Once these parameters are chosen, the transport of the drug out of the device and through the tissue surrounding it is computed (713).

Following the computation, it is assessed (714) whether the resulting drug distribution is acceptable in the sense of matching the target limits chosen in 750. If it is not, the steps from selection of device position (710) to assessment of the predicted drug distribution (714) are repeated. If the predicted result is acceptable, the physical device is configured to the selected design (711) and placed (715) in the position selected (710). The time stepping of the therapeutic infusion schedule (712) is selected and the current time is updated (720). The current state of the infusion process within the subject is scanned (721) and a check is made (730) of whether the state matches the prediction (713) made earlier. If it does, then it is further checked (737) whether the injection schedule (712) has been completed; if it is not, the steps from time step update (720) to checking the match with the prediction (730) are repeated. If the injection schedule (712) has been completed, the injection process is concluded (740). If the current scanned state (721) does not match the prediction (713), a new prediction is generated (731) and a check is made (732) of whether the new prediction (731) is acceptable. If it is, the steps from time step update (720) to check of acceptability (732) are repeated. If the new prediction (731) is not acceptable, it is determined (734) whether a revised infusion schedule may yield more acceptable results. If a suitable revised schedule is found, this is chosen as the new infusion schedule (733) and the process reverts to time step selection and update (720). If no such revised schedule is found, an emergency stop (738) is arrived at and the infusion process is concluded (740).

What is claimed is:

1. A method for delivering material to tissue within a patient comprising inserting a device into a patient, wherein the device comprises a tube for delivering materials to internal tissue of a patient, said tube comprising a lumen for carrying the material, holes from said lumen to an exterior surface of the tube, and control elements for modifying flow rates of the material from said lumen through said holes, at least some control elements being remotely controllable from outside the patient and controlling a rate of flow of the material through a hole in the tube by controlling the control element wherein a planned position of the tube within the body is shown on a computer display of a computer system, and a medical practitioner uses a graphical interface to specify regions where high concentration of the delivered material is respectively desired or to be avoided, or where it is essential to limit pressure above background, edema or the time for which either occurs, and the computer system uses a model of the diffusion and transport process to define a set of holes and membranes that will result in satisfying these criteria, and then the designed set of holes and/or membranes are provided in a tube.

2. The process of claim 1 where the graphical interface uses a mouse, tablet or similar 2D input device to control an image on a screen in which slices of a body scan are displayed.

3. The process of claim 1 where the graphical interface uses a 3d input device to control an image in a stereographic display in which volume-rendered images of a body scan are displayed.

4. The method of claim 1 wherein said tube is assembled from at least two cylindrical subunits, each of said at least two cylindrical subunits having different flow properties through surfaces of the cylinders.

5. The method of claim 1 wherein imaging is used at the time of insertion of a catheter to confirm that the catheter has been placed in the planned position.

6. A method for delivering material to tissue within a patient comprising inserting a device into a patient, wherein the device comprises a tube for delivering materials to internal tissue of a patient, said tube comprising a lumen for carrying the material, holes from said lumen to an exterior surface of the tube, and control elements for modifying flow rates of the material from said lumen through said holes, at least some control elements being remotely controllable from outside the patient and controlling a rate of flow of the material through a hole in the tube by controlling the control element where a medical practitioner selects the number, size and placement of the holes, and the penetrability and placement of internal membranes, selection based on computer predictions as to the distribution of delivered material when material in a chosen concentration is passed down the tube with a selected time course of pressure or of pumping rate.

7. The method of claim 6 where said tube is assembled from a set of cylindrical sub-units, at least two of said cylindrical subunits having different arrangements of side holes.

8. The method of claim 6 where said tube is assembled from a set of cylindrical sub-units, at least two of said cylindrical subunits having different and control elements.

9. A method for delivering material to tissue within a patient comprising inserting a device into a patient, wherein the device comprises a tube for delivering materials to internal tissue of a patient, said tube comprising a lumen for carrying the material, holes from said lumen to an exterior surface of the tube, and control elements for modifying flow rates of the material from said lumen through said holes, at least some control elements being remotely controllable from outside the patient and controlling a rate of flow of the material through a hole in the tube by controlling the control element wherein a medical practitioner specifies only the region in which a rigid tube is to be placed, together with regions where piercing by the tube would be unacceptable, and a computer defines an entry path which achieves ancillary criteria including at least one parameter selected from the group consisting of a) minimal damage en route to the target region, and b) minimal time spent drilling through hole to open pathway.

10. A method for delivering material to tissue within a patient comprising inserting a device into a patient, wherein the device comprises a tube for delivering materials to internal tissue of a patient, said tube comprising a lumen for carrying the material, holes from said lumen to an exterior surface of the tube, and control elements for modifying flow rates of the material from said lumen through said holes, at least some control elements being remotely controllable from outside the patient and controlling a rate of flow of the material through a hole in the tube by controlling the control element, and remotely controlling a rate of flow of the material through a hole in the tube by remotely controlling the control element.

11. A method for delivering material to tissue within a patient comprising inserting a device into a patient, wherein the device comprises a tube for delivering materials to internal tissue of a patient, said tube comprising a lumen for carrying the material, holes from said lumen to an exterior surface of the tube, and control elements for modifying flow rates of the material from said lumen through said holes, at least some control elements being remotely controllable from outside the patient and controlling a rate of flow of the material through a hole in the tube by controlling the control element wherein a real-time visualization of distributed-material is used to confirm that distribution of material is occurring in accordance with a predetermined plan, and where deviation from said predetermined plan is found, a controller modifies the pumping rate or pressure if appropriate.

12. The method of claim 10 wherein said controller is a computer.

* * * * *